(12) United States Patent
Vincent

(10) Patent No.: US 7,279,006 B2
(45) Date of Patent: Oct. 9, 2007

(54) INTRAOCULAR LENS AND INJECTOR FOR THE SAME

(75) Inventor: Patrice Vincent, Mevoisins (FR)

(73) Assignee: Laboratoire de Contactologie Appliquee-LCA, Chartres (FR)

( * ) Notice: Subject to any disclaimer, the term of this patent is extended or adjusted under 35 U.S.C. 154(b) by 64 days.

(21) Appl. No.: 10/547,247

(22) PCT Filed: Mar. 26, 2004

(86) PCT No.: PCT/FR2004/000767

§ 371 (c)(1),
(2), (4) Date: Aug. 26, 2005

(87) PCT Pub. No.: WO2004/089251

PCT Pub. Date: Oct. 21, 2004

(65) Prior Publication Data

US 2006/0173540 A1  Aug. 3, 2006

(30) Foreign Application Priority Data

Apr. 1, 2003  (FR) ................................. 03 04019

(51) Int. Cl.
*A61F 2/16* (2006.01)
*A61F 9/00* (2006.01)

(52) U.S. Cl. ..................... 623/6.46; 623/6.12; 606/107

(58) Field of Classification Search ...... 623/6.12–6.49; 606/107
See application file for complete search history.

(56) References Cited

U.S. PATENT DOCUMENTS

| 4,242,762 A | | 1/1981 | Tennant | |
|---|---|---|---|---|
| 5,074,877 A | | 12/1991 | Nordan | |
| 5,562,676 A | * | 10/1996 | Brady et al. | 606/107 |
| 6,066,172 A | * | 5/2000 | Huo et al. | 623/6.56 |
| 6,461,384 B1 | | 10/2002 | Hoffmann et al. | |
| 2002/0055777 A1 | * | 5/2002 | Cumming et al. | 623/6.37 |
| 2003/0018386 A1 | * | 1/2003 | Laguette et al. | 623/6.46 |
| 2005/0222578 A1 | * | 10/2005 | Vaquero | 606/107 |

FOREIGN PATENT DOCUMENTS

| WO | WO83/00998 A | 3/1983 |
|---|---|---|
| WO | WO 00/49974 A | 8/2000 |
| WO | WO 00/53124 A | 9/2000 |

OTHER PUBLICATIONS

International Preliminary Examination Report for PCT/FR2004/000767; Issued Jun. 17, 2005.

\* cited by examiner

*Primary Examiner*—Suzette Gherbi
(74) *Attorney, Agent, or Firm*—Holland & Hart LLP

(57) ABSTRACT

An injectable intraocular lens (10) made of flexible material, said lens (10) having an optical portion (11) that is preferably of approximately circular shape, said injectable intraocular lens being characterized in that it also has two side flats (15) provided on opposite edges of the optical portion (11), said flats (15) forming an angle relative to each other.

13 Claims, 2 Drawing Sheets

INTRAOCULAR LENS AND INJECTOR FOR THE SAME

Figure 1:
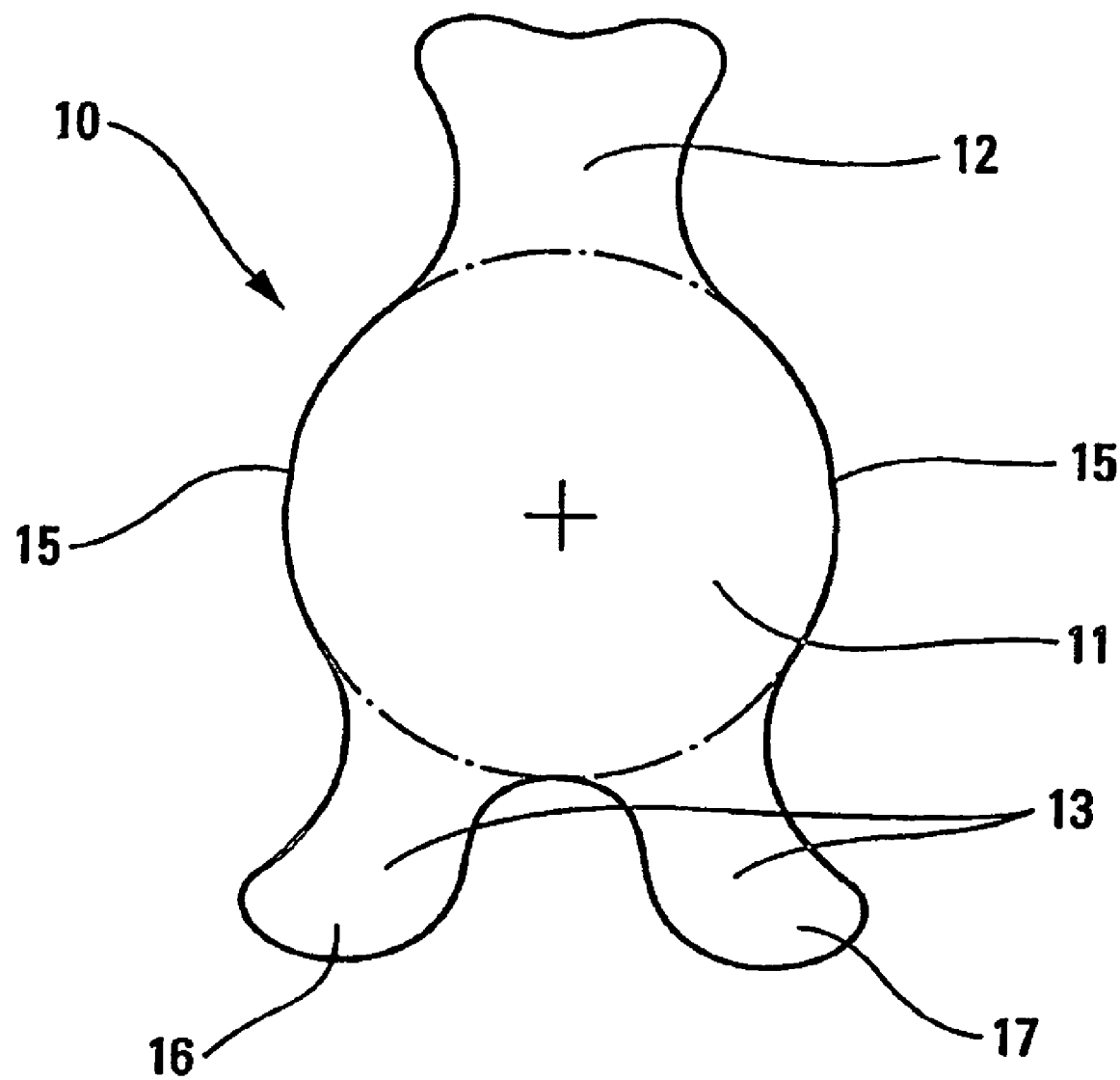

The present invention relates to an injectable intraocular lens and to an injector for injecting such a lens.

In known manner, an intraocular lens serves to replace the lens of a patient undergoing a cataract operation. The haptic of the intraocular lens is the portion that is situated outside the optical portion and that serves to hold the lens in position inside the eye of the patient. Usually, the lower haptic is the haptic portion that is inserted first, since the incision is usually situated frontally and, during the operation, the surgeon is placed behind the head of the patient who is prone. The upper haptic, which is placed last, remains the haptic portion that is closer to the incision.

The concept of using an injector emerged with the concept of using intraocular lenses made of a flexible, mechanically deformable material. That development is a response to the use of small incisions for cataract surgery, the width of such incisions often being limited to about 3 millimeters (mm). It should be possible for the end piece of the injector to pass through the incision without it being necessary to widen it.

Numerous models of injectors exist for injecting intraocular lenses. In most cases, the intraocular lens is folded by an accessory device such as a cartridge having a flap, a slide, or an abutment rib, so that the role of the piston is confined to final pushing through the endpiece.

The cylindrical endpiece of the injector is of mean inside diameter (in the range 1.5 mm to 4 mm) smaller than the diameter (in the range 5 mm to 7 mm) of the optical portion of the intraocular lens. The idea of causing the lens to pass through a progressively tapering segment that is therefore conical to some extent has already been disclosed in prior patents, in particular in Documents WO 00/49974 and WO 02/00970.

One of the main difficulties of that technique consists in ensuring that the lens remains in alignment in the system throughout the stage of diametrical compression of the lens.

In particular, the substantially circular shape of the optical portion of the lens can give rise to the lens being displaced transversely and thus undergoing loss of axial alignment. Furthermore, the lower haptic of the lens is disposed downstream from the optical portion in the direction in which the lens is dispensed, and therefore might rub prematurely against the conical inside wall of the injector, which can destabilize the lens or cause the lower haptic to be folded over onto the optical portion, thereby jeopardizing ejection of said lens.

An object of the present invention is to provide an intraocular lens and an associated injector that do not reproduce the above-mentioned drawbacks.

A particular object of the present invention is to provide such a lens and such an injector that operate safely and reliably, without any risk of the lens jamming in the injector while it is being dispensed.

Another object of the invention is to provide such a lens and such an injector that are simple and inexpensive to manufacture.

To these ends, the present invention provides an injectable intraocular lens made of flexible material, said lens having an optical portion that is preferably of approximately circular shape, said lens also having two side flats provided on opposite edges of the optical portion, said flats forming an angle relative to each other.

Advantageously, said optical portion is symmetrical about a central longitudinal axis of the lens.

Advantageously, each of said flats has a length of at least 0.5 mm, and preferably of about 1 mm.

Advantageously, said lens has a lower haptic of transverse dimension smaller than the transverse dimension of the optical portion.

Advantageously, said lens has an upper haptic.

Advantageously, said upper haptic has two side elements.

The present invention also provides an intraocular lens injector having a cylindrical main body and a conical body portion opening out into a dispensing portion of small size, said injector including a lens as defined above.

Advantageously, prior to being dispensed, said lens is disposed in said injector without being deformed.

Advantageously, the angle formed by said flats of the lens corresponds to the angle formed by the wall of the conical portion of the injector.

Advantageously, prior to dispensing, the lower haptic of the lens is spaced apart from the wall of the conical body portion by at least 0.2 mm, and preferably about 0.5 mm.

Advantageously, said injector has a piston adapted to move said lens from the cylindrical body portion, through the conical body portion, to the dispensing portion.

Advantageously, said piston co-operates with said upper haptic and/or with said optical portion of the lens.

The present invention also provides a method of dispensing an intraocular lens by means of an injector, said method being characterized in that it comprises the following steps: providing an injector having a cylindrical main portion and a conical body portion opening out into a dispensing portion of small size, and a piston mounted to move in said injector; disposing an intraocular lens in non-deformed manner in said injector, said lens having an optical portion provided with two side flats, said flats forming an angle corresponding to the angle formed by the wall of the conical body portion of the injector; and moving the lens towards the dispensing portion by means of the piston, said flats sliding against the conical wall, thereby causing the optical portion to fold and then the remainder of the lens to fold, while maintaining the axial alignment of the lens.

Figure 2:
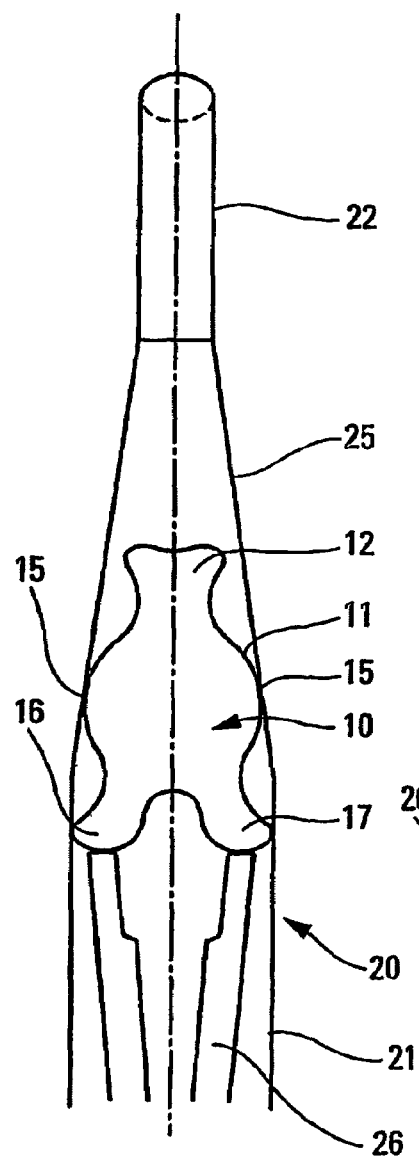
Figure 3:
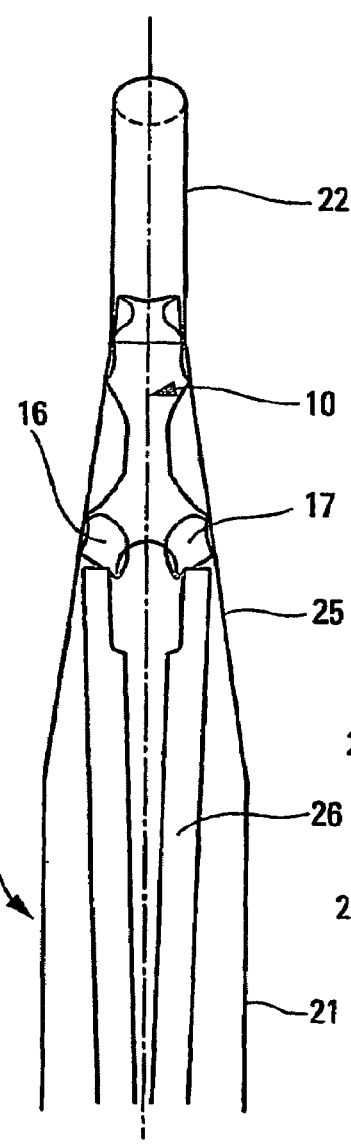
Figure 4:
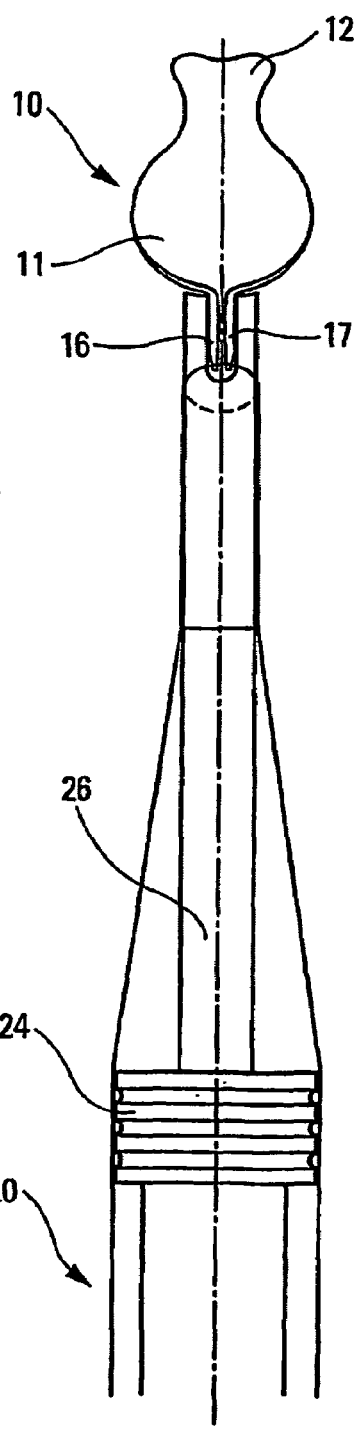

Other characteristics and advantages of the present invention appear more clearly from the following detailed description of an embodiment of the present invention, given with reference to the accompanying drawings, which are given by way of non-limiting example, and in which:

FIG. 1 is a diagrammatic section view of an embodiment of an intraocular lens of the present invention; and FIGS. 2 to 4 show diagrammatic views of an embodiment of the injector of the present invention, respectively at the start, during, and at the end of dispensing of the intraocular lens of FIG. 1.

FIG. 1 diagrammatically shows an intraocular lens of the invention.

The intraocular lens 10 comprises an optical portion 11 that is preferably approximately circular, and that is adapted to fold as soon as it is compressed about its diameter. The lens 10 advantageously further comprises a lower haptic 12 which is disposed downstream in the direction in which the lens moves inside the body of the injector and/or an upper haptic 13 which can co-operate with said piston 24. Said upper haptic 13 can be made up of two side elements 16, 17 that are advantageously symmetrical.

In the invention, the optical portion 11 of the lens has two flats 15 situated on the edge of the optical portion, on opposite sides thereof. As can be seen in FIG. 1, said flats 15 form an angle relative to each other. Preferably, the lens, and in particular the optical portion 11, are symmetrical about the central longitudinal axis of the lens. The minimum length of each flat 15 is 0.5 mm, and preferably said length is about 1 millimeter.

Advantageously, said lens 10 is made in one piece and of a flexible material. Preferably, the transverse dimension of the lower haptic 12 is smaller than the transverse dimension of the optical portion 11. The object is to prevent the lower haptic 12 from starting to fold inside the injector before the optical portion starts folding, which might prevent the lens from being dispensed. By way of example, the optical portion 11 can have a width of 5.4 mm, and the lower haptic 12 can have a width of 3 mm.

FIGS. 2 to 4 show a particular embodiment of the injector 20 of the present invention. In this embodiment, the injector includes a body constituted by a cylindrical main portion 21, by a cylindrical dispensing portion 22, which is of cross-section smaller than the cross-section of the main portion 21, and by a conical body portion 25 which connects the main portion 21 to said dispensing portion 22. The taper of the conical portion 25, i.e. the angle formed by the wall relative to the central longitudinal axis of the injector advantageously corresponds to the angle of the flats of the lens. The main portion 21 is adapted to contain the lens 10 in the non-deformed state, as shown in FIG. 2.

Documents WO 00/49974 and WO 02/00870 are mentioned herein by way of reference as regards the shape and operation of the injector 20.

The piston 24 can have one or more branches 26, in particular two branches in the example shown. Said branches 26 can move towards each other when the piston 24 slides inside the conical portion 25.

Initially, the lens 10 is disposed such that each of the two branches 26 of the piston 24 faces a respective side element 16, 17 of the upper haptic 13. The optical portion 11 is merely guided when the piston is actuated, and the lower haptic 12, which is narrow, is engaged without contact in the conical portion 25 of the injector 20.

When pressure is exerted on the piston 24, the lens 10 is firstly moved in translation without being deformed, until the two flats 15 of the optical portion 11 come into contact with the conical portion 25. By continuing to exert pressure on the piston 20, the optical portion 11 is caused to starting folding, the wall of the conical portion 25 guiding the flats 15 so as to keep the lens 10 in axial alignment. In folding, the optical portion 11 is almost rolled up while being in contact with the wall of the conical portion 25. The lower haptic 12 then starts folding, when it comes into contact with the conical portion 25, by following the movement of the optical portion 11. The smaller radial dimension of the lower haptic 12 prevents said lower haptic from folding before the optical portion 11.

After folding, the lens 10 is pushed into the dispensing portion 22.

At the end of pushing, as shown in FIG. 4, the optical portion 11 is redeployed inside the eye of the patient, and the side elements 16, 17 of the upper haptic 13 are pressed against each other.

The present invention is described above with reference to an advantageous embodiment of it, but clearly, it is not limited to this embodiment. In particular, the haptics can be of any shape, and said haptics are not necessarily made in one piece with the optical portion of the lens. The shape of the upper haptic 13 shown in the drawing is particularly well adapted to transmitting the thrust via a multi-branch piston. Naturally, the piston can be of any type, and could co-operate with the upper haptic, with the optical portion, or even with both of them. In addition, lenses having fitted loop-type haptics, or one-piece lenses of various shapes, e.g. with C-shaped strands, shuttles, haptics with four bearing points, or the like, are also covered by the present invention.

Other modifications can be made by the person skilled in the art without going beyond the ambit of the present invention, as defined by the accompanying claims.

The invention claimed is:

1. An injectable intraocular lens (10) made of flexible material, said lens (10) having an optical portion (11) that is approximately circular shape, said injectable intraocular lens (10) being characterized in that it has two side flats (15) provided on opposite edges of the optical portion (11), said two side flats (15) forming an angle relative to each other.

2. A lens according to claim 1, in which said optical portion (11) is symmetrical about a central longitudinal axis of the lens (10).

3. A lens according to claim 1, in which each of said two side flats (15) has a length of at least 0.5 mm.

4. A lens according to claim 1, in which said lens (10) has a lower haptic (12) of transverse dimension smaller than a transverse dimension of the optical portion (11).

5. A lens according to claim 1, in which said lens (10) has an upper haptic (13).

6. A lens according to claim 5, in which said upper haptic (13) has two side elements (16, 17).

7. An assembly comprising an intraocular lens injector (20) and an intraocular lens (10), said assembly being characterized in that said injector (20) has a cylindrical main body (21) and a conical body portion (25) opening out into a dispensing portion (22) of small size, and in that said lens (10) is made of flexible material, said lens (10) having an optical portion (11) that is approximately circular shape, said injectable intraocular lens (10) being characterized in that it has two side flats (15) provided on opposite edges of the optical portion (11), said two side flats (15) forming an angle relative to each other.

8. An assembly according to claim 7, in which, prior to being dispensed, said lens (10) is disposed in said injector without being deformed.

9. An assembly according to claim 7, in which the angle formed by said two side flats (15) of the lens (10) corresponds to an angle formed by a wall of the conical portion (25) of the injector (20).

10. An assembly according to claim 7, in which, prior to dispensing, a lower haptic (12) of the lens (10) is spaced apart from a wall of the conical body portion (25) by at least 0.2 mm.

11. An assembly according to claim 7, in which said injector (20) has a piston (24) adapted to move said lens (10) from the cylindrical body portion (21), through the conical body portion (25), to the dispensing portion (22).

12. An assembly according to claim 11, in which said piston (24) co-operates with a upper haptic (13) and/or with said optical portion (11) of the lens (10).

13. A method of dispensing an intraocular lens (10) by means of an injector, said method being characterized in that it comprises the following steps:
  providing an injector (20) having a cylindrical main portion (21) and a conical body portion (25) opening out into a dispensing portion (22) of small size, and a piston (24) mounted to move in said injector;
  disposing an intraocular lens (10) in a non-deformed manner in said injector (20), said lens (10) having an optical portion (11) provided with two side flats (15), said two side flats (15) forming an angle corresponding to the angle formed by a wall of the conical body portion (25) of the injector (20); and
  moving the lens (10) towards the dispensing portion (22) by means of the piston (24), said two side flats (15) sliding against the conical wall (25), thereby causing the optical portion (11) to fold and then a remainder of the lens (10) to fold, while maintaining an axial alignment of the lens (10).

* * * * *